US011130939B2

(12) United States Patent
Hou et al.

(10) Patent No.: US 11,130,939 B2
(45) Date of Patent: Sep. 28, 2021

(54) BACTERIA FOR DEGRADING ETHYLENE OXIDE AND USES THEREOF

(71) Applicants: Chio Kang Medical, Inc., Palo Alto, CA (US); QIAOKANG BIOTECH (GUANGDONG) CO., LTD., Guangzhou (CN)

(72) Inventors: Dongxin Hou, Guangzhou (CN); Jianlong Xue, Guangzhou (CN); Jiali Lin, Guangzhou (CN); Xin Yin, Guangzhou (CN); Yecheng He, Guangzhou (CN); Shengwei Hu, Guangzhou (CN); Qinghua Xiao, Guangzhou (CN); Liqing Zhu, Guangzhou (CN); Lixiong Feng, Guangzhou (CN)

(73) Assignees: CHIO KANG MEDICAL, INC., Palo Alto, CA (US); QIAOKANG BIOTECH (GUANGDONG) CO., LTD., Guangdong (CN)

( * ) Notice: Subject to any disclaimer, the term of this patent is extended or adjusted under 35 U.S.C. 154(b) by 0 days.

(21) Appl. No.: 17/012,797

(22) Filed: Sep. 4, 2020

(65) Prior Publication Data
US 2021/0230535 A1    Jul. 29, 2021

Related U.S. Application Data

(63) Continuation of application No. PCT/CN2020/101141, filed on Jul. 9, 2020.

(30) Foreign Application Priority Data

Jan. 20, 2020   (CN) .......................... 202010063308.6
Jan. 20, 2020   (CN) .......................... 202010064633.4
Jan. 20, 2020   (CN) .......................... 202010064688.5
Jan. 20, 2020   (CN) .......................... 202010065467.X

(51) Int. Cl.

| | |
|---|---|
| C02F 1/00 | (2006.01) |
| C12N 1/20 | (2006.01) |
| C12N 1/36 | (2006.01) |
| C02F 3/34 | (2006.01) |
| B01D 53/84 | (2006.01) |
| B01D 53/72 | (2006.01) |
| A62D 3/02 | (2007.01) |
| C12N 1/26 | (2006.01) |
| A62D 101/28 | (2007.01) |
| C02F 101/34 | (2006.01) |
| C12R 1/02 | (2006.01) |
| C12R 1/125 | (2006.01) |
| C12R 1/225 | (2006.01) |

(52) U.S. Cl.
CPC ................ *C12N 1/36* (2013.01); *A62D 3/02* (2013.01); *B01D 53/72* (2013.01); *B01D 53/84* (2013.01); *C02F 3/34* (2013.01); *C12N 1/20* (2013.01); *C12N 1/205* (2021.05); *A62D 2101/28* (2013.01); *B01D 2251/95* (2013.01); *C02F 2101/34* (2013.01); *C12R 2001/02* (2021.05); *C12R 2001/125* (2021.05); *C12R 2001/225* (2021.05)

(58) Field of Classification Search
None
See application file for complete search history.

(56) References Cited

U.S. PATENT DOCUMENTS

| | | |
|---|---|---|
| 1,954,056 A | 4/1934 | Miller |
| 2,586,670 A | 2/1952 | Lambertsen |
| 2,817,689 A | 12/1957 | White |
| 3,022,054 A | 2/1962 | Kotzebue |
| 3,572,391 A | 3/1971 | Hirsch et al. |
| 3,598,543 A | 8/1971 | Crosby et al. |
| 3,844,739 A | 10/1974 | Alfrey, Jr. |
| 3,961,920 A | 6/1976 | Gilbert |
| 3,997,633 A | 12/1976 | Leva et al. |
| 4,112,054 A | 9/1978 | Feingold et al. |
| 4,119,539 A | 10/1978 | Ettel et al. |
| 4,134,425 A | 1/1979 | Gussefeld et al. |

(Continued)

FOREIGN PATENT DOCUMENTS

| | | |
|---|---|---|
| CN | 1223166 A | 7/1999 |
| CN | 1397474 A | 2/2003 |

(Continued)

OTHER PUBLICATIONS

Perez-Cano, Francisco J; et al; "In vitro immunomodulatory activity of Lactobacillus fermentum CECT5716 and Lactobacillus salivarius CECT5713: two probiotic strains isolated from humanbreast milk" Immunobiology, 215, 996-1004, 2010 (Year: 2010).*

(Continued)

*Primary Examiner* — David W Berke-Schlessel
(74) *Attorney, Agent, or Firm* — Adsero IP

(57) ABSTRACT

The present disclosure relates to strains for degrading ethylene oxide and degradation agents comprising the same, wherein the strains are *Acetobacter peroxydans* EO-01 strain with Deposit number of CGMCC No. 18431; *Lactobacillus fermentum* EO-02 strain with Deposit number of CGMCC No. 18432; or *Bacillus subtilis* EO-03 strain with Deposit number of CGMCC No. 18433. The strains are capable of safely and efficiently degrading ethylene oxide. The present disclosure also provides a method for purifying and producing strains that can degrade ethylene oxide, and a method for biodegrading ethylene oxide.

5 Claims, 8 Drawing Sheets
Specification includes a Sequence Listing.

(56) References Cited

U.S. PATENT DOCUMENTS

| | | |
|---|---|---|
| 4,243,636 A | 1/1981 | Shiraki et al. |
| 4,274,954 A | 6/1981 | Blair |
| 4,301,113 A | 11/1981 | Alguire et al. |
| 4,517,167 A | 5/1985 | Popescu et al. |
| 4,549,363 A | 10/1985 | Buonicore |
| 4,831,196 A | 5/1989 | Buonicore et al. |
| 5,084,075 A | 1/1992 | Sircar |
| 5,204,075 A | 4/1993 | Jain et al. |
| 5,270,000 A | 12/1993 | Goldner et al. |
| 5,283,035 A | 2/1994 | Karthaus et al. |
| 5,290,345 A | 3/1994 | Osendorf et al. |
| 5,511,409 A | 4/1996 | Knaebel |
| 5,522,808 A | 6/1996 | Skalla |
| 5,607,652 A | 3/1997 | Hellmuth et al. |
| 5,641,455 A | 6/1997 | Rosenlund et al. |
| 5,702,669 A | 12/1997 | Green |
| 5,741,470 A | 4/1998 | Wenzler |
| 5,755,857 A | 5/1998 | Acharya et al. |
| 5,779,773 A | 7/1998 | Cam et al. |
| 5,883,199 A | 3/1999 | McCarthy et al. |
| 5,964,927 A | 10/1999 | Graham et al. |
| 6,156,101 A | 12/2000 | Naheiri |
| 6,684,648 B2 | 2/2004 | Faqih |
| 6,743,402 B2 | 6/2004 | Shimakawa |
| 7,625,535 B2 | 12/2009 | Yamaguchi |
| 8,110,156 B2 | 2/2012 | Ricciardi et al. |
| 8,431,085 B2 | 4/2013 | Froderberg et al. |
| 9,616,143 B2 | 4/2017 | Snyder et al. |
| 10,987,443 B1 | 4/2021 | Hu et al. |
| 2001/0033838 A1 | 10/2001 | Farmer |
| 2002/0046569 A1 | 4/2002 | Faqih |
| 2002/0197194 A1 | 12/2002 | Machado et al. |
| 2004/0229340 A1 | 11/2004 | Kawai |
| 2006/0236860 A1 | 10/2006 | Sumida et al. |
| 2006/0249027 A1 | 11/2006 | Adolphsen et al. |
| 2007/0209383 A1 | 9/2007 | Hutton |
| 2008/0078289 A1 | 4/2008 | Sergi et al. |
| 2008/0080999 A1 | 4/2008 | Bondar |
| 2008/0289591 A1 | 11/2008 | Tessier et al. |
| 2010/0196194 A1 | 8/2010 | Voeten et al. |
| 2010/0291169 A1 | 11/2010 | Toreki et al. |
| 2011/0265644 A1 | 11/2011 | Swami et al. |
| 2012/0031268 A1 | 2/2012 | Yaghi et al. |
| 2012/0298207 A1 | 11/2012 | Woelk et al. |
| 2014/0119989 A1 | 5/2014 | Hayashi |
| 2014/0251130 A1 | 9/2014 | Sprinkle et al. |
| 2014/0290162 A1 | 10/2014 | Tanimoto |
| 2016/0010883 A1 | 1/2016 | Jornitz et al. |
| 2016/0130489 A1 | 5/2016 | Gilmour |
| 2017/0056813 A1 | 3/2017 | McMahon et al. |
| 2019/0076776 A1 | 3/2019 | Mahecha-Botero et al. |
| 2019/0151791 A1 | 5/2019 | Awadh et al. |
| 2019/0175971 A1 | 6/2019 | Moore et al. |
| 2020/0148655 A1 | 5/2020 | Duff et al. |

FOREIGN PATENT DOCUMENTS

| | | |
|---|---|---|
| CN | 101224381 A | 7/2008 |
| CN | 101549241 A | 10/2009 |
| CN | 101773762 A | 7/2010 |
| CN | 201632182 U | 11/2010 |
| CN | 102173384 A | 9/2011 |
| CN | 102219642 A | 10/2011 |
| CN | 102302791 A | 1/2012 |
| CN | 102921570 A | 2/2013 |
| CN | 202802975 U | 3/2013 |
| CN | 202933710 U | 5/2013 |
| CN | 203183363 U | 9/2013 |
| CN | 103386141 A | 11/2013 |
| CN | 103394109 A | 11/2013 |
| CN | 103394278 A | 11/2013 |
| CN | 103657383 A | 3/2014 |
| CN | 103667014 A | 3/2014 |
| CN | 103706233 A | 4/2014 |
| CN | 203507806 U | 4/2014 |
| CN | 203564952 U | 4/2014 |
| CN | 103800926 A | 5/2014 |
| CN | 103801190 A | 5/2014 |
| CN | 103908688 A | 7/2014 |
| CN | 203749877 U | 8/2014 |
| CN | 203750388 U | 8/2014 |
| CN | 203750389 U | 8/2014 |
| CN | 104014227 A | 9/2014 |
| CN | 104275085 A | 1/2015 |
| CN | 104307008 A | 1/2015 |
| CN | 204261680 U | 4/2015 |
| CN | 204447972 U | 7/2015 |
| CN | 104815535 A | 8/2015 |
| CN | 104946557 A | 9/2015 |
| CN | 105132060 A | 12/2015 |
| CN | 105327665 A | 2/2016 |
| CN | 105664822 A | 2/2016 |
| CN | 105462903 A | 4/2016 |
| CN | 205300112 U | 6/2016 |
| CN | 210721130 U | 6/2016 |
| CN | 106139199 A | 11/2016 |
| CN | 106421844 A | 2/2017 |
| CN | 106475021 A | 3/2017 |
| CN | 106582126 A | 4/2017 |
| CN | 106754585 | 5/2017 |
| CN | 107058179 A | 8/2017 |
| CN | 206443946 U | 8/2017 |
| CN | 206535551 U | 10/2017 |
| CN | 107460146 A | 12/2017 |
| CN | 206853397 U | 1/2018 |
| CN | 107677016 A | 2/2018 |
| CN | 207169397 U | 4/2018 |
| CN | 207187436 U | 4/2018 |
| CN | 107988095 A | 5/2018 |
| CN | 207356290 U | 5/2018 |
| CN | 207745676 U | 8/2018 |
| CN | 207913454 U | 9/2018 |
| CN | 108607511 A | 10/2018 |
| CN | 208047841 U | 11/2018 |
| CN | 208218734 U | 12/2018 |
| CN | 109294942 A | 2/2019 |
| CN | 109382064 A | 2/2019 |
| CN | 208448985 U | 2/2019 |
| CN | 208893903 U | 5/2019 |
| CN | 110106086 A | 8/2019 |
| CN | 110145747 A | 8/2019 |
| CN | 110302634 A | 10/2019 |
| CN | 110404485 A | 11/2019 |
| CN | 110461371 A | 11/2019 |
| CN | 209662917 U | 11/2019 |
| CN | 110833754 A | 2/2020 |
| CN | 210021633 U | 2/2020 |
| CN | 210088451 U | 2/2020 |
| CN | 111117931 A | 5/2020 |
| CN | 111117932 A | 5/2020 |
| CN | 111154684 A | 5/2020 |
| CN | 111154687 A | 5/2020 |
| DE | 4236622 C1 | 3/1994 |
| EP | 0130319 A2 | 1/1985 |
| EP | 0350677 A1 | 1/1990 |
| EP | 1238718 A1 | 9/2002 |
| EP | 1302478 A1 | 4/2003 |
| EP | 2883598 A1 | 6/2015 |
| GB | 1472091 A | 4/1977 |
| JP | 2008114210 A | 5/2008 |
| JP | 2010259648 A | 11/2010 |
| JP | 2013172790 A | 10/2016 |
| JP | 2016221497 A | 12/2016 |
| WO | WO 2006115199 A1 | 11/2006 |
| WO | WO2011002277 A1 | 1/2011 |
| WO | WO 2012013197 A2 | 2/2012 |
| WO | WO-2019-136504 A1 | 7/2019 |
| WO | WO 2019236249 A1 | 12/2019 |

OTHER PUBLICATIONS

Bao, Yan; et al; "Screening of potential probiotic properties of Lactobacillus fermentum isolated from traditional dairy products"

(56) References Cited

OTHER PUBLICATIONS

Food Control, 21, 695-701, 2010 (Year: 2010).*
U.S. Appl. No. 17/012,769, TrackOne Bypass CON Application, filed Sep. 4, 2020, 75 pages.
U.S. Appl. No. 17/012,810, TrackOne Bypass CON Application, filed Sep. 4, 2020, 73 pages.
U.S. Appl. No. 17/012,828, TrackOne Bypass CON Application, filed Sep. 4, 2020, 86 pages.
U.S. Appl. No. 17/012,843, TrackOne Bypass CON Application, filed Sep. 4, 2020, 67 pages.
International Search Report and Written Opinion dated Dec. 16, 2020 in PCT/CN2020/101142, 11 pages.
International Search Report and Written Opinion, in PCT/CN2020/101140 dated Dec. 21, 2020, 11 pages.
International Search Report and Written Opinion, in PCT/CN2020/100143 dated Dec. 21, 2020, 9 pages.
International Search Report and Written Opinion, in PCT/CN2020/100125 dated Dec. 23, 2020, 9 pages.
International Search Report and Written Opinion, in. PCT/CN2020/100115 dated Dec. 16, 2020, 11 pages.
International Search Report and Written Opinion, in. PCT/CN2020/100119 dated Dec. 17, 2020, 9 pages.
International Search Report and Written Opinion, in PCT/CN2020/100144 dated Dec. 18, 2020, 10 pages.
Kahm et al., 2018 "Lyapunov exponents with Model Predictive Control for exothermic batch reactors" IFAC—PapersOnline, 51, 417-422.
Brown, et al., (1997) J. Ag and Food Chem. 3(45): 955-961, "Degradation of Thifensulfuron Methyl in Soil: Role of Microbial Carboxyesterase Activity".
Danko, et al., (2008) Proc. Biochem. 43:517-521, "Involvement of carbon dioxide in the aerobic biodegradation of ethylene oxide, ethene, and vinyl chloride".
Derwent-Acc-No. 2017-83105H (2017) "New Bacillus coagulans i.e. Bacillus coagulans Daoduo 4 and method (M1) for screening the B. coagulans". Abstract only, 1 pg.
Fei, et al. (2006) Annals Micro. 3(56):201-205, "Identification of *Enterococcus* sp. from midgut of silkworm based on biochemical and 16S rDNA sequencing analysis".
International Search Report and Written Opinion dated Oct. 28, 2020 in PCT/CN2020/101143, 10 pages.
International Search Report and Written Opinion dated Oct. 21, 2020 in PCT/CN2020/101141, 12 pages.
International Search Report and Written Opinion dated Oct. 27, 2020 in PCT/CN2020/101138, 11 pages.
International Search Report and Written Opinion dated Oct. 28, 2020 in PCT/CN2020/101144, 10 pages.
International Search Report and Written Opinion dated Oct. 28, 2020 in PCT/CN2020/101139, 11 pages.

Khatiwala, et al. (2008) J. Polym. Environ. 16:61-67, "Biodegradation of poly($\varepsilon$-caprolactone)(PCL) film by alcaligenes faecalis".
Liao, et al., (2001) Environ. Tech. 22:165-173, "Decomposition of ethylene oxide in the RF plasma environment".
Poelarends, et al., (1999) J. Bact. 7(181):2050-2058, "Degradation of 1, 2-Dibromoethane by *Mycobacterium* sp. Strain GP1".
Shin, et al., (2016) Anaerobe 39:14-18, "*Clostridium kogasensis* sp. nov., a novel member of the genus *Clostridium*, isoloated from soil under a corroded gas pipeline".
Sutton, et al. (2018) F1000 Research 7:1-26, "*Enterobacter hormaechei* subsp. *hoffmannii* subsp. nov., *Enterobacter hormaechei* subsp. *xiangfangensis* comb. nov., *Enterobacter roggenkampii* sp. nov., and Enterobacter muelleri is a later heterotypic synonym of Enterobacter asburiae based on computational analysis of sequenced Enterobacter genomes".
Taylor, et al., (2010) Appl. Micro. Biotech. 87:2293-2302, "Extending the alkene substrate range of vinyl chloride utilizing *Nocardioides* sp. strain JS614 with ethene oxide".
U.S. Appl. No. 17/012,857, TrackOne Bypass CON Application filed Sep. 4, 2020, 148 pages.
U.S. Appl. No. 17/002,500, TrackOne Bypass CON Application filed Aug. 25, 2020, 61 pages.
U.S. Appl. No. 17/002,523, TrackOne Bypass CON Application filed Aug. 25, 2020, 72 pages.
U.S. Appl. No. 17/002,529, TrackOne Bypass CON Application filed Aug. 25, 2020, 64 pages.
U.S. Appl. No. 17/002,540, TrackOne Bypass CON Application filed Aug. 25, 2020, 89 pages.
U.S. Appl. No. 17/004,730, TrackOne Bypass CON Application filed Aug. 27, 2020, 77 pages.
U.S. Appl. No. 17/012,864, TrackOne Bypass CON Application filed Sep. 4, 2020, 78 pages.
U.S. Appl. No. 17/004,903, TrackOne Bypass CON Application filed Aug. 27, 2020, 67 pages.
U.S. Appl. No. 17/004,930, TrackOne Bypass CON Application filed Aug. 27, 2020, 80 pages.
U.S. Appl. No. 17/004,971, TrackOne Bypass CON Application filed Aug. 27, 2020, 75 pages.
Yin, et al., (2016) Int. J. Hydrogen Energy, "Characterization and hydrogen production performance of a novel strain Enterococcus faecium INET2 isolated from gamma irradiated sludge". pp. 22793-22801; issue 41.
International Search Report & Written Opinion for PCT/CN2020/100113 as prepared by the Chinese International Searching Authority dated Mar. 31, 2021, 10 pages.
International Search Report & Written Opinion for PCT/CN2020/100122 as prepared by the Chinese International Searching Authority dated Mar. 26, 2021, 11 pages.
International Search Report & Written Opinion for PCT/CN2020/100120 as prepared by the Chinese International Searching Authority dated Mar. 31, 2021, 10 pages.

\* cited by examiner

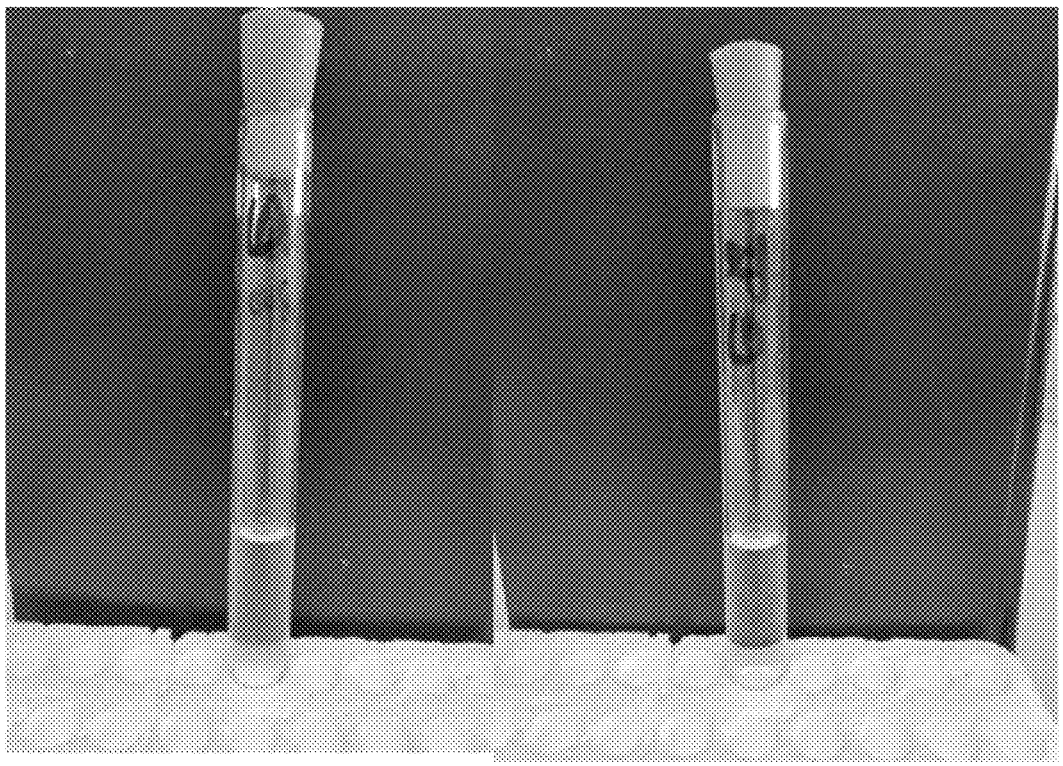
FIG. 4A                    FIG. 4B
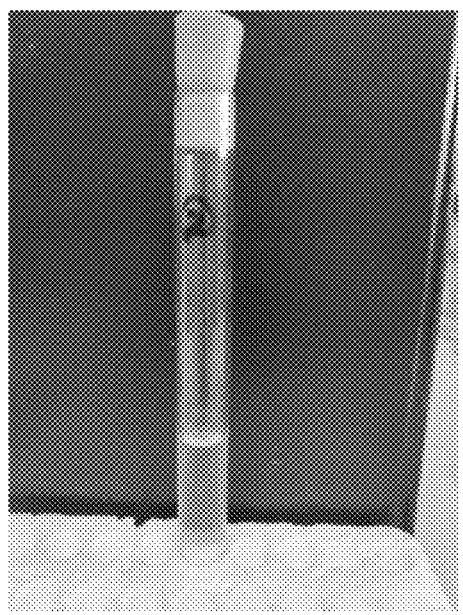          
FIG. 5A                    FIG. 5B

BACTERIA FOR DEGRADING ETHYLENE OXIDE AND USES THEREOF

CROSS-REFERENCE TO RELATED PATENT APPLICATIONS

This application is a Bypass Continuation of PCT/CN2020/101141, filed Jul. 9, 2020, which application claims the benefit of Chinese Patent Application No. 202010065467.X, filed on Jan. 20, 2020, Chinese Patent Application No. 202010064633.4, filed on Jan. 20, 2020, Chinese Patent Application No. 202010064688.5, filed on Jan. 20, 2020 and Chinese Patent Application No. 202010063308.6, filed on Jan. 20, 2020, the entire contents of which are incorporated herein by reference in their entirety for all purposes.

TECHNICAL FIELD

The present disclosure relates to the field of microbial technology, and more particularly to bacteria for degrading ethylene oxide and uses thereof.

SEQUENCE STATEMENT

Incorporated by reference herein in its entirety is the Sequence Listing entitled "1211_CK02_ST25_PCT" created Jun. 1, 2020, size of 10.4 kilobytes.

BACKGROUND

Among the most important petrochemical products in the modern industries, ethylene oxide (EO) is widely used in the industries, such as laundry and dyeing, medicine, textile, papermaking, automobile, oil exploitation and refining, and the like. For example, ethylene oxide can be used as a broad-spectrum and highly effective sterilizing agent due to its ability of killing most bacteria, spores, viruses and fungi and has a strong penetrating power to reach depth of an article, therefore playing an irreplaceable role in medical sterilization and related industries. However, ethylene oxide is extremely active, flammable and explosive, and is also recognized as a carcinogen globally. Ethylene oxide, if discharged directly without disposal, will pose a great threat to the environment and biological safety, and thus should be subjected to harmless disposal.

For example, at present, there are two main ways for industrial disposal of ethylene oxide in waste gas. One way is reaction of ethylene oxide waste gas with sulfuric acid. However, sulfuric acid has a lower saturation degree of absorption to ethylene oxide, resulting in a low efficiency, and by-products that are difficult to dispose are generated, increasing the cost for disposal. The other way is oxidization of ethylene oxide waste gas in an oxidation reacting furnace, which requires very strict control of technical parameters and is subject to high risks of explosion during the disposal.

Therefore, there is an urgent and long-felt need for those skilled in the art to find a safe and effective way disposal of ethylene oxide.

SUMMARY

In view of this, the present disclosure provides a strain capable of effectively degrading ethylene oxide. The strain is capable of safely and efficiently degrading ethylene oxide, for example, those present in contaminants, such as sewage, sludge, exhaust gas, from industries, such as petrochemical industry, sewage disposal, and medical sterilization, with low cost and without production of harmful or difficult-to-handle by-products. Therefore, the strain may be widely used in industries.

In one aspect of the present disclosure, there is provided a strain capable of degrading ethylene oxide, which is: *Acetobacter peroxydans* EO-01 with Deposit number of CGMCC No. 18431; *Lactobacillus fermentum* EO-02 with Deposit number of CGMCC No. 18432; or *Bacillus subtilis* EO-03 with Deposit number of CGMCC No. 18433.

In one of the aspects of the present disclosure, there is provided a strain capable of degrading ethylene oxide, which is: an *Acetobacter peroxydans* strain comprising the 16S rDNA sequence of SEQ ID NO: 3; a *Lactobacillus fermentum* strain comprising the 16S rDNA sequence of SEQ ID NO: 4; or a *Bacillus subtilis* strain comprising the 16S rDNA sequence of SEQ ID NO: 5. These strains can effectively degrade ethylene oxide.

In a further aspect of the present disclosure, there is provided a degradation agent for degrading ethylene oxide, comprising at least one strain selected from the group consisting of *Acetobacter peroxydans* EO-01 with Deposit number of CGMCC No. 18431; *Lactobacillus fermentum* EO-02 with Deposit number of CGMCC No. 18432; *Bacillus subtilis* EO-03 with Deposit number of CGMCC No. 18433; the *Acetobacter peroxydans* strain comprising the 16S rDNA sequence of SEQ ID NO: 3; a *Lactobacillus fermentum* strain comprising the 16S rDNA sequence of SEQ ID NO: 4; or a *Bacillus subtilis* strain comprising the 16S rDNA sequence of SEQ ID NO: 5.

In some of the embodiments, the strain capable of degrading ethylene oxide in the degradation agent has a concentration of at least $10^{10}$ cfu/mL, e.g. from $10^{10}$ cfu/mL to $10^{12}$ cfu/mL.

In some of the embodiments, the degradation agent further comprises other strains capable of degrading ethylene oxide, for example, *Alcaligenes faecalis* EO-05 strain, deposited on Aug. 29, 2019 at China General Microbiological Culture Collection Center, with Deposit number of CGMCC No. 18435 disclosed in CN111117932A; *Enterococcus faecium* EO-04 strain, deposited on Aug. 29, 2019 at China General Microbiological Culture Collection Center, with Deposit number of CGMCC No. 18434 disclosed in CN111117930A; an *Alcaligenes faecalis* strain comprising the 16S rDNA sequence of SEQ ID NO: 6, an *Enterococcus faecium* strain comprising the 16S rDNA sequence of SEQ ID NO: 7; and the like.

In one of the aspects of the present disclosure, it provides a method for preparing a degradation agent for degrading ethylene oxide, comprising: inoculating a strain of the invention into a Sabouraud culture medium, and incubating the inoculated Sabouraud culture medium thereby obtaining the degradation agent. In some aspects, the strain is inoculated into Sabouraud culture medium. In some aspects, the strain is incubated for 24-48 hours of incubation at 37° C. and 200 rpm.

In one of the aspects of the present disclosure, it provides a method for decreasing the amount of ethylene oxide in sample, comprising adding to a sample comprising ethylene oxide an amount of a pure culture of an *Acetobacter peroxydans*, *Lactobacillus fermentum*, or *Bacillus subtilis* strain bacterium, allowing the bacterium to degrade the ethylene oxide, thereby decreasing the amount of ethylene oxide, wherein the 16S rDNA sequence of the *Acetobacter peroxydans* strain bacterium is SEQ ID NO: 3; the 16S rDNA sequence of the *Lactobacillus fermentum* strain bacterium is SEQ ID NO: 4; or the 16S rDNA sequence of the *Bacillus subtilis* strain bacterium is SEQ ID NO: 5.

In a further aspect of the method, the *Acetobacter peroxydans, Lactobacillus fermentum*, or *Bacillus subtilis* strain bacterium is capable of using ethylene oxide as a carbon source and is capable of growing normally with ethylene oxide as the main carbon source in the culture.

In a further aspect of the method, the *Acetobacter peroxydans* strain bacterium is *Acetobacter peroxydans* EO-01 with the Deposit Number of CGMCC No. 18431; the *Lactobacillus fermentum* strain bacterium is *Lactobacillus fermentum* strain EO-02 with the Deposit Number of CGMCC No. 18432; or the *Bacillus subtilis* strain bacterium is *Bacillus subtilis* strain EO-03 with the Deposit Number of CGMCC No. 18433.

In a further aspect of the present disclosure, there is also provided a method for purifying ethylene oxide-degrading potential bacteria, comprising:

incubating a suspension containing at least one original strain selected from the group consisting of *Acetobacter peroxydans, Lactobacillus fermentum*, and *Bacillus subtilis* into a first enrichment medium to obtain a bacterial suspension, wherein the first enrichment medium is liquid glucose-tryptone medium containing ethylene oxide;

inoculating and incubating the bacterial suspension into a screening and purification medium to obtain an ethylene oxide-degrading predominant strain, wherein the screening and purification medium is glucose-tryptone agar medium containing ethylene oxide; and inoculating and incubating the ethylene oxide-degrading predominant strain into a second enrichment medium to obtain an ethylene oxide-degrading potential bacteria, wherein the second enrichment medium is liquid glucose-tryptone medium containing no ethylene oxide.

In one embodiment, the method comprises mixing sewage or sludge containing the original strain with phosphate buffer, and filtering for removal of precipitate so as to obtain the suspension.

In one embodiment, the first enrichment medium is prepared as follows: sterilizing liquid glucose-tryptone medium, cooling the medium to room temperature, and adding liquid ethylene oxide to the medium. The liquid glucose-tryptone medium contains 5 g/L casein trypsin digest, 5 g/L animal tissue pepsin digest, and 40 g/L glucose, and has pH 5.4-5.8.

In one embodiment, the screening and purification medium is prepared as follows: sterilizing glucose-tryptone agar medium, cooling the medium to 50° C. to 55° C., and adding liquid ethylene oxide to the medium. The glucose-tryptone agar medium contains 5 g/L casein trypsin digest, 5 g/L animal tissue pepsin digest, 40 g/L glucose, and 15 g/L agar, and has pH 5.4-5.8.

In one embodiment, the second enrichment medium is prepared as follows: sterilizing glucose-tryptone medium, and cooling the medium to room temperature. The second enrichment medium contains 5 g/L casein trypsin digest, 5 g/L animal tissue pepsin digest, and 40 g/L glucose, and has pH 5.4-5.8.

In one embodiment, the suspension is incubated in the first enriched enrichment medium having a low concentration of ethylene oxide for 24 to 48 hours, and the bacterial suspension is incubated on the screening and purification medium plate having a low concentration of ethylene oxide for at least 24 hours. The low concentration of ethylene oxide in the first enriched enrichment medium and the screening and purification medium plate may be range from 10 mg/L to 500 mg/L, e.g., 100 mg/L.

In one embodiment, the ethylene oxide-degrading predominant strain is incubated in the second enrichment medium for at least 24 hours.

In further aspect of the present disclosure, there is also provided a method for producing a strain for degrading ethylene oxide, comprising:

inoculating at least one original strain selected from the group consisting of *Acetobacter peroxydans, Lactobacillus fermentum*, and *Bacillus subtilis* into ethylene oxide-tolerance acclimation mediums for subculture, to obtain an ethylene oxide-degrading predominant strain, wherein the ethylene oxide-tolerance acclimation mediums are glucose-peptone agar mediums containing ethylene oxide with an serially increasing concentration during subculture; and inoculating the ethylene oxide-degrading predominant strain into ethylene oxide-degradation acclimation mediums for subculture, wherein the ethylene oxide-degradation acclimation mediums are glucose-peptone agar mediums containing ethylene oxide and a carbon source with a serially decreasing concentration in the ethylene oxide-degradation acclimation mediums during subculture.

In one embodiment, the concentration of ethylene oxide serially increases from 100 mg/L to 800 mg/L during subculture.

In one embodiment, the concentration of the carbon source in the ethylene oxide-degradation acclimation mediums serially decreases from 20 g/L to 0 g/L during subculture.

In one embodiment, the original strain is incubated at a temperature from 25° C. to 37° C. in the ethylene oxide-tolerance acclimation medium.

In one embodiment, the ethylene oxide-degrading predominant strain is incubated at a temperature from 25° C. to 37° C. in ethylene oxide-degradation acclimation mediums.

In one embodiment, the original strain is subcultured in ethylene oxide-tolerance acclimation mediums containing 0 mg/L to 100 mg/L, 100 mg/L to 200 mg/L, 200 mg/L to 500 mg/L, 500 mg/L to 800 mg/L ethylene oxide for 24 to 48 hours serially and respectively.

In one embodiment, the original strain is subcultured in ethylene oxide-tolerance acclimation medium plates containing ethylene oxide having a gradually increasing concentration in an incubator at a temperature from 25° C. to 37° C. serially and respectively for 24 to 48 hours; and finally incubated in an ethylene oxide-tolerance acclimation medium plate containing 500 mg/L~800 mg/L ethylene oxide to obtain the ethylene oxide-degrading predominant strain.

In one embodiment, the original strain is subcultured in the ethylene oxide-tolerance acclimation mediums containing 100 mg/L, 200 mg/L, 500 mg/L, 800 mg/L ethylene oxide serially and respectively.

In one embodiment, the ethylene oxide-degrading predominant strain is obtained by: inoculating the original strain into the first ethylene oxide-tolerance acclimation medium plate containing 100 mg/L ethylene oxide for subculture, and incubating the first plate in an incubator at 37° C. for 24 to 48 hours; picking a first single colony with a largest radius on the first plate and inoculating the first single colony into the second ethylene oxide-tolerance acclimation medium plate with 100 to 200 mg/L ethylene oxide for subculture, and incubating the second plate in an incubator at 37° C. for 24 to 48 hours; picking a second single colony with a largest radius on the second plate and inoculating the second single colony into the third ethylene oxide-tolerance acclimation medium plate with 200 to 500 mg/L ethylene oxide for subculture, and incubating the third plate in an incubator at 37° C. for 24 to 48 hours; picking a third single colony with a largest radius on the third plate and inoculating the third single colony into the fourth ethylene oxide-tolerance acclimation medium plate with 500 to 800 mg/L ethylene oxide for subculture, and incubating the fourth plate in an incubator at 37° C. for 24 to 48 hours; finally picking a fourth single colony with a largest radius on the fourth ethylene oxide-tolerance acclimation medium plate containing 500 to 800 mg/L ethylene oxide to obtain the ethylene oxide-degrading predominant strain.

In one embodiment, the ethylene oxide-tolerance acclimation mediums are prepared as follows: adding liquid ethylene oxide into a sterilized glucose-peptone agar medium to a final concentration from 100 mg/L to 800 mg/L, wherein the ethylene oxide-tolerance acclimation mediums contain 10 g/L peptone, 40 g/L glucose, and 15 g/L agar, and has pH 5.4-5.8.

In one embodiment, the sterilized glucose-peptone agar mediums are heated to melt, cooled to 50° C. to 56° C., and mixed with liquid ethylene oxide.

In one embodiment, the ethylene oxide-degrading predominant strain is serially subcultured in the ethylene oxide-degradation acclimation mediums containing 20 g/L 12 g/L, 4 g/L, and 0 g/L the carbon source for 24 to 48 hours.

In one embodiment, the ethylene oxide-degradation acclimation mediums have glucose as the carbon source.

In one embodiment, the ethylene oxide-degrading predominant strain is inoculated into the ethylene oxide-degradation acclimation medium plates having 500 mg/L to 800 mg/L ethylene oxide and a carbon source with a serially decreasing concentration, and subcultured in an incubator at a temperature from 25° C. to 37° C. for 24 to 48 hours respectively and serially; and picking a single colony with a largest radius to obtain the strain for degrading ethylene oxide.

In one embodiment, the strain for degrading ethylene oxide is obtained as follows: inoculating the ethylene oxide-degrading predominant strain into the first ethylene oxide-degradation acclimation medium plate containing 800 mg/L ethylene oxide and 20 g/L carbon source, and incubating the first plate in an incubator at 37° C. for 24 to 48 hours; picking a first single colony with a largest radius on the first plate, inoculating the first single colony into the second ethylene oxide-degradation acclimation medium plate containing 800 mg/L ethylene oxide and 12 g/L carbon source, and incubating the second plate in an incubator at 37° C. for 24 to 48 hours; picking a second single colony with a largest radius on the second plate, inoculating the second single colony into the third ethylene oxide-degradation acclimation medium plate containing 800 mg/L ethylene oxide and 4 g/L carbon source, and incubating the third plate in an incubator at 37° C. for 24 to 48 hours; picking a third single colony with a largest radius on the third plate, inoculating the third single colony into the fourth ethylene oxide-degradation acclimation medium plate containing 800 mg/L ethylene oxide and 0 g/L carbon source, and incubating the fourth plate in an incubator at 37° C. for 24 to 48 hours; finally picking a fourth single colony with a largest radius on the fourth ethylene oxide-degradation acclimation medium plate containing 800 mg/L ethylene oxide and 0 g/L carbon source to obtain the strain for degrading ethylene oxide.

In one embodiment, the ethylene oxide-degradation acclimation mediums are prepared as follows: adding liquid ethylene oxide into sterilized glucose-peptone agar mediums, wherein the glucose-peptone agar mediums contain 10 g/L peptone, 0 g/L to 20 g/L glucose, and 15 g/L agar, and has pH 5.4-5.8.

In one embodiment, the sterilized glucose-peptone agar medium is heated to melt, cooled to 50° C. to 56° C., and mixed with the liquid ethylene oxide.

In a further aspect of the present disclosure, there is also provided a method for biodegrading ethylene oxide, comprising:

degrading ethylene oxide using at least one strain selected from the group consisting of, or a degradation agent comprising at least one strain selected from the group consisting of:

*Acetobacter peroxydans* EO-01 with Deposit number of CGMCC No. 18431;

*Lactobacillus fermentum* EO-02 with Deposit number of CGMCC No. 18432; and

*Bacillus subtilis* EO-03 with Deposit number of CGMCC No. 18433.

In some embodiments, the method comprises degrading ethylene oxide in sewage, sludge, and/or exhaust gas. The sewage, sludge and/or waste may be derived from industrial (e.g., petroleum and derivatives related industries), medical (e.g., ethylene oxide sterilizing agent), and others.

In some embodiments of the methods, the degradation rate is at least 10%, 15%, 20%, 25%, 30%, 35%, 40%, 50%, 60%, 70%, 75%, 80%, 90%, 95%, 100%, 125%, 150%, 200%, 250%, 300%, 350%, 400%, 450%, 500%, 550%, 600%, 650%, 700%, 750%, 800%, 850%, 900%, 1000%, 1100%, 1200%, 1300%, 1400%, or 1500% greater relative to the degradation rate of ethylene oxide in the absence of a strain of the invention, namely *Acetobacter peroxydans* EO-01 with Deposit number of CGMCC No. 18431; *Lactobacillus fermentum* EO-02 with Deposit number of CGMCC No. 18432; *Bacillus subtilis* EO-03 with Deposit number of CGMCC No. 18433; the *Acetobacter peroxydans* strain comprising the 16S rDNA sequence of SEQ ID NO: 3; a *Lactobacillus fermentum* strain comprising the 16S rDNA sequence of SEQ ID NO: 4; or a *Bacillus subtilis* strain comprising the 16S rDNA sequence of SEQ ID NO: 5.

In some embodiments, the method comprises incubating the strain in liquid Sabouraud medium to a concentration from $10^{10}$ cfu/mL to $10^{12}$ cfu/mL, so as to obtain an activation liquid for degrading ethylene oxide.

In one embodiment, the method comprises the concentration of the strain for degrading ethylene oxide ranges from $10^8$ cfu/mL to $10^{10}$ cfu/mL.

The present disclosure provides strains capable of degrading ethylene oxide and uses thereof. The strains can be used for disposal of ethylene oxide pollutants, such as sewage, sludge or exhaust gas from ethylene oxide related industrial or medical. The outstanding tolerance and remarkable degradability of the strain on ethylene oxide having a high concentration can allow such a difficult-to-handle ethylene oxide having a high concentration to be degraded without providing other carbon sources, thereby greatly improving the capacity for harmless disposal of ethylene oxide in industrial. For example, *Acetobacter peroxydans* EO-01 degrades 400 mg/L ethylene oxide with a degradation rate of 63.82%, and 800 mg/L ethylene oxide with a degradation rate of 51.28%; *Lactobacillus fermentum* EO-02 degrades 400 mg/L ethylene oxide with a degradation rate of 83.93%, and 800 mg/L ethylene oxide with a degradation rate of 52.54%; and *Bacillus subtilis* EO-03 degrades 400 mg/L ethylene oxide with a degradation rate of 72.96%, and 800 mg/L ethylene oxide with a degradation rate of 57.19%.

The deposit information of the three strains for degrading ethylene oxide mentioned disclosed herewith is as follows:

The *Acetobacter peroxydans* EO-01 with Deposit Number of CGMCC No. 18431, the *Lactobacillus fermentum* EO-02 with Deposit Number of CGMCC No. 18432 and the *Bacillus subtilis* EO-03 with Deposit Number of CGMCC No. 18433 were deposited on Aug. 29, 2019 at China General Microbiological Culture Collection Center (CGMCC) with the deposit address being Institute of Microbiology of Chinese Academy of Sciences, NO. 1 West Beichen Road, Beijing 100101, China.

BRIEF DESCRIPTION OF DRAWINGS

FIGS. 4A and 4B show bacterial colony growth of *Acetobacter peroxydans* EO-01 strain (FIG. 4A) after the inducted acclimation of Example 2, and (FIG. 4B) before the inducted acclimation of Example 2 in a liquid Sabouraud induction medium with 800 mg/L ethylene oxide after growing at a constant temperature of 37° C. for 48 hours in a comparative experiment of ethylene oxide degradation in Example 3 of the present disclosure.

FIGS. 5A and 5B show bacterial colony growth of *Lactobacillus fermentum* EO-02 strain (FIG. 5A) after the inducted acclimation of Example 2, and (FIG. 5B) before the inducted acclimation of Example 2 in a liquid Sabouraud induction medium with 800 mg/L ethylene oxide after growing at a constant temperature of 37° C. for 48 hours in a comparative experiment of ethylene oxide degradation in Example 3 of the present disclosure.

DETAILED DESCRIPTION OF EMBODIMENTS

Figure 1A:
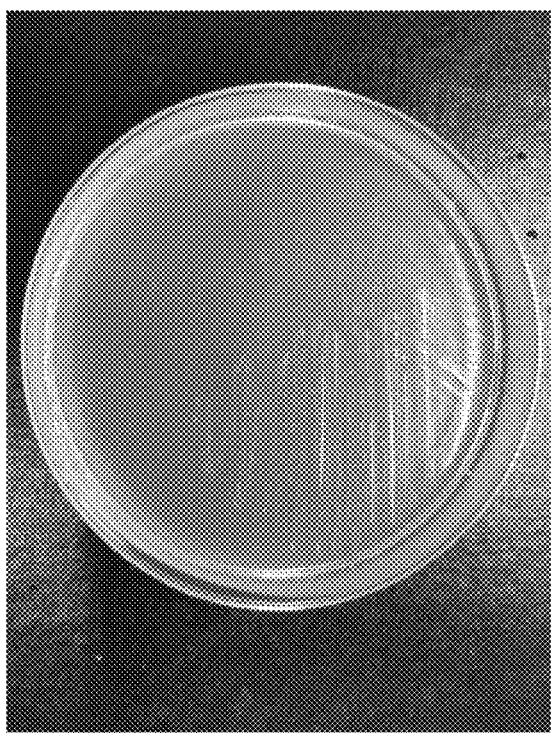
FIGS. 1A to 1C show bacterial colony growth of the EO-degrading potential bacteria in the second enrichment medium after growing for 48 hours at a constant temperature of 37° C., wherein the EO-degrading potential bacteria were, FIG. 1A, *Acetobacter peroxydans* EO-01 original strain, FIG. 1B, *Lactobacillus fermentum* EO-02 original strain, and FIG. 1C *Bacillus subtilis* EO-03 original strain obtained by the enrichment, purification and screening processes according to Example 1 of the present disclosure.

Detailed description will be given below with referral to the accompanying figures to facilitate understanding of the present disclosure. Preferred embodiments are shown in the figures. However, the present disclosure may be implemented in various ways, without being limited to the examples presented in the description. The purpose of these embodiments is merely for illustration and better comprehension of the present disclosure.

Unless otherwise defined, all the technical and scientific terms herein shall be understood as the same meaning with those commonly accepted by a person skilled in the art. Such terms, as used herein, are for the purpose of describing specific embodiments of, without limiting, the present disclosure. The term "and/or" as used herein refers to any and all combinations of one or more items recited.

Enrichment, Purification, Screening and Identification of Strains with Ethylene Oxide Degradation Ability Below is an example of enrichment, purification, screening, and identification of strains with ethylene oxide degradation ability.

Example 1

I. Enrichment, Purification and Screening

A sample of the sludge mixture was collected at the sewage outlet of a suburban sewage disposal plant in Guangzhou, Guangdong Province, and used for the enrichment, purification and screening experiments of this example.

A first enrichment medium was prepared as follows: 40 g of glucose, 5 g of casein trypsin digest, and 5 g of animal tissue pepsin digest were mixed, adjusted to pH 5.4-5.8, filled to 1000 mL with distilled water and thoroughly mixed. Portions of 250 ml of the prepared medium were added to 500 mL Erlenmeyer flasks, sterilized at 121° C. for 20 min, and cooled to room temperature. Pure liquid ethylene oxide was cooled down in an ice bath before 28 μL was taken and injected into the sterilized medium by a sealed syringe, providing 100 mg/L ethylene oxide in the medium complying with the national emission standard, to obtain the first enrichment medium.

The screening and purification medium was prepared as follows: 40 g of glucose, 5 g of casein trypsin digest, 5 g of animal tissue pepsin digest and 15 g of agar were mixed, adjusted to pH of 5.4, and filled to 1000 mL with distilled water and thoroughly mixing. Portions of 250 ml of the prepared medium were added into 500 mL Erlenmeyer flasks, sterilized at 121° C. for 20 minutes, and cooled to about 50-56° C. 28 μL of liquid ethylene oxide was injected into the sterilized medium by a sealed syringe to obtain the screening and purification medium.

A second enrichment medium was prepared as follows: 40 g of glucose, 5 g of casein trypsin digest, and 5 g of animal tissue pepsin digest were mixed, adjusted to pH 5.4-5.8, filled to 1000 mL with distilled water and thoroughly mixed. Portions of 250 ml of the prepared medium were added into 500 mL Erlenmeyer flasks, sterilized at 121° C. for 20 minutes, and cooled to room temperature to obtain the second enrichment medium.

10.0 g of the sludge mixture sample was weighed, added with 100 mL of 0.03 mol/L phosphate buffer, well mixed, allowed to stand for 120 min for clarification, and filtered to remove large particles of sediment and obtain a suspension.

1 mL of the suspension was added into 10 mL of the first enrichment medium in each of four test tubes and placed in a shaker for oxygen-consuming enrichment culture for 24 to 48 hours (200 rpm, 37° C.).

The predominant strains from the first enrichment medium were streaked on the screening and purification medium for isolation to obtain ethylene oxide-degrading predominant strains.

The ethylene oxide-degrading predominant strains were incubated in the second enrichment medium for 24 hours to obtain three EO-degrading potential strains, designated as the EO-01 original strain, EO-02 original strain and EO-03 original strain, respectively. The three EO-degrading potential strains were preserved at −80° C. using the glycerin preservation method (medium: 50% glycerol=1:1).

At 48 hours of incubation in the screening and purification medium, the colony morphology of the EO-01 original strain was milky white needle-like petites with gray or off-white cells, a smooth and moist surface, a round shape, regular edges, a colony diameter of about 1.0 mm, and no pigment. The colony morphology of the EO-02 original strain was milky white needle-like petites, colorless and transparent, with a smooth and moist surface, a round shape, regular edges, a colony diameter from 0.5 mm to 1.0 mm, and no pigment. The colony morphology of the EO-03 original strain was off-white or light yellow and opaque, with a rough surface, uneven edges, high viscosity, a colony diameter about 4.0-5.0 mm, and no pigment.

Example 2 Characterization and Identification of Ethylene Oxide-Degrading Bacteria Strains The following identification methods were used:

Morphological characterization, including observation of colony morphology, microscopic morphology, culture characteristics and Gram staining;

Physiological and biochemical characterization, including nutrition type, nitrogen and carbon source utilization capacity, and biochemical tests;

Molecular biological characterization (16s rDNA sequencing), including the procedure of bacterial culture, bacterial DNA extraction, PCR amplification, 16s rDNA sequencing and sequence alignment analysis, wherein the primer pair for PCR amplification was as follows:

Upstream primer 27F: 5'-AGAGTTT-GATCCTGGCTCAG-3', as shown in SEQ ID NO: 1;

and

Downstream primer 1492R: 5'-GGTTACCTTGT-TACGACTT-3', as shown in SEQ ID NO: 2.

The above characterization and identification methods are well known to those skilled in the art.

Figure 1B:
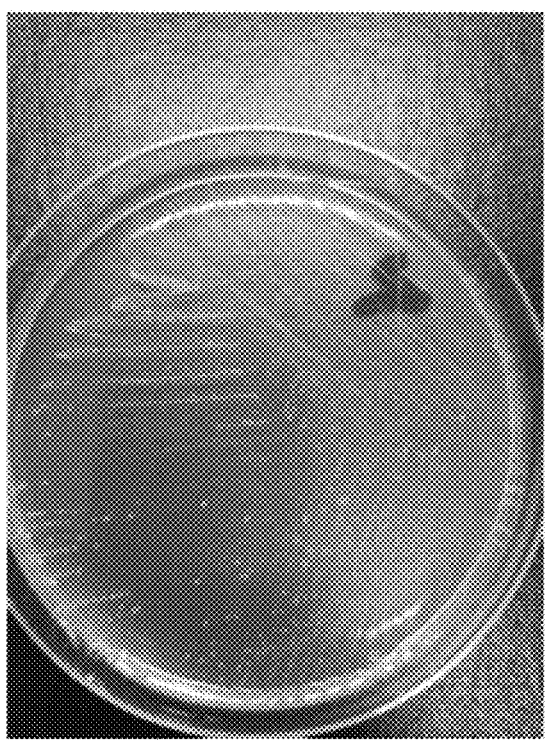
Figure 1C:
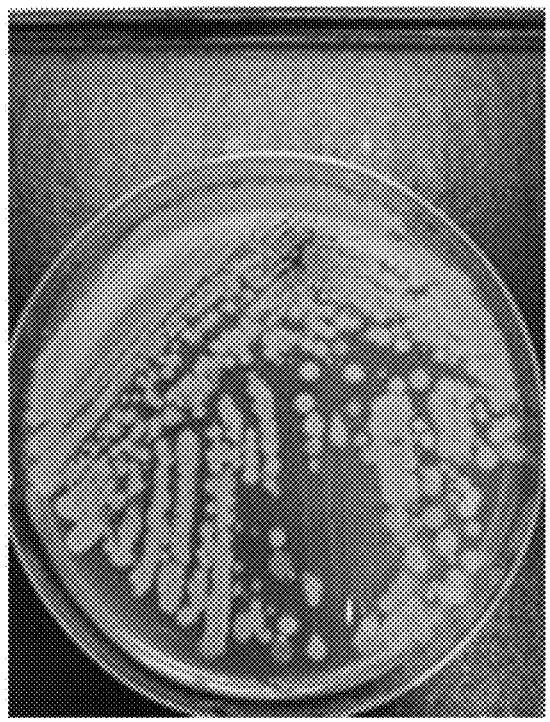
Figure 2A:
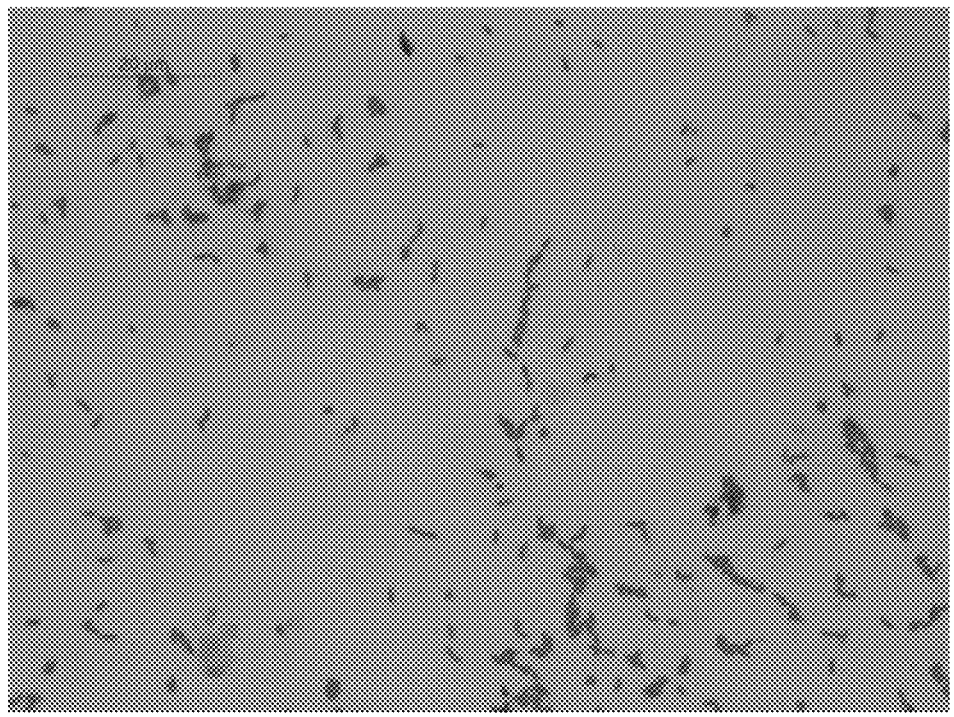
FIGS. 2A to 2C show Gram staining results of the EO-degrading potential bacteria, wherein the EO-degrading potential bacteria are, FIG. 2A, *Acetobacter peroxydans* EO-01 original strain, FIG. 2B. *Lactobacillus fermentum* EO-02 original strain, and FIG. 2C *Bacillus subtilis* EO-03 original strain obtained by the enrichment, purification and screening processes according to Example 1 of the present disclosure.
Figure 2B:
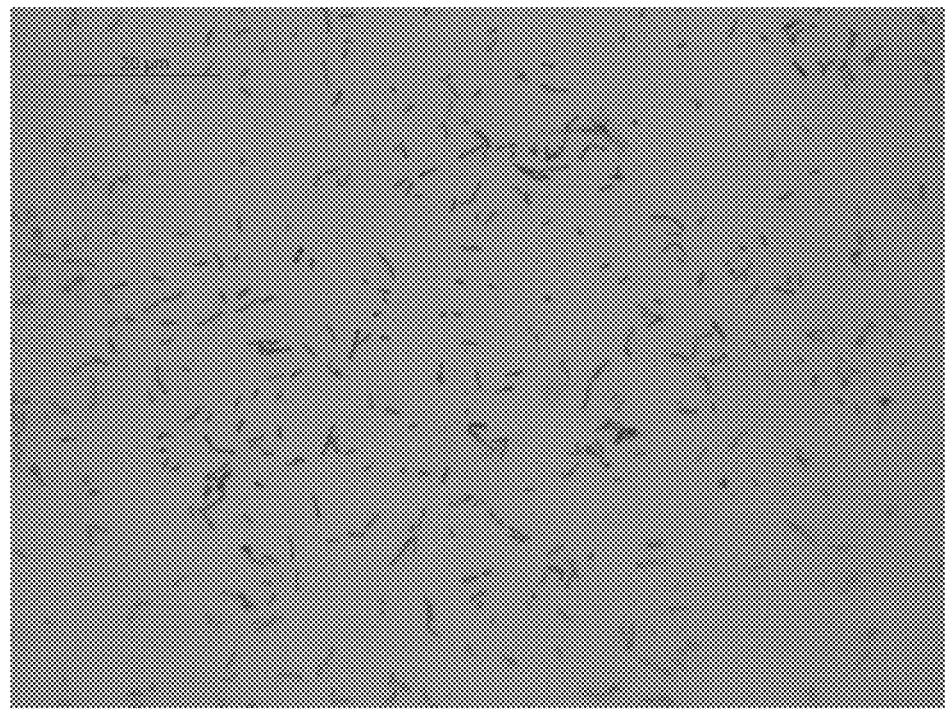
Figure 2C:
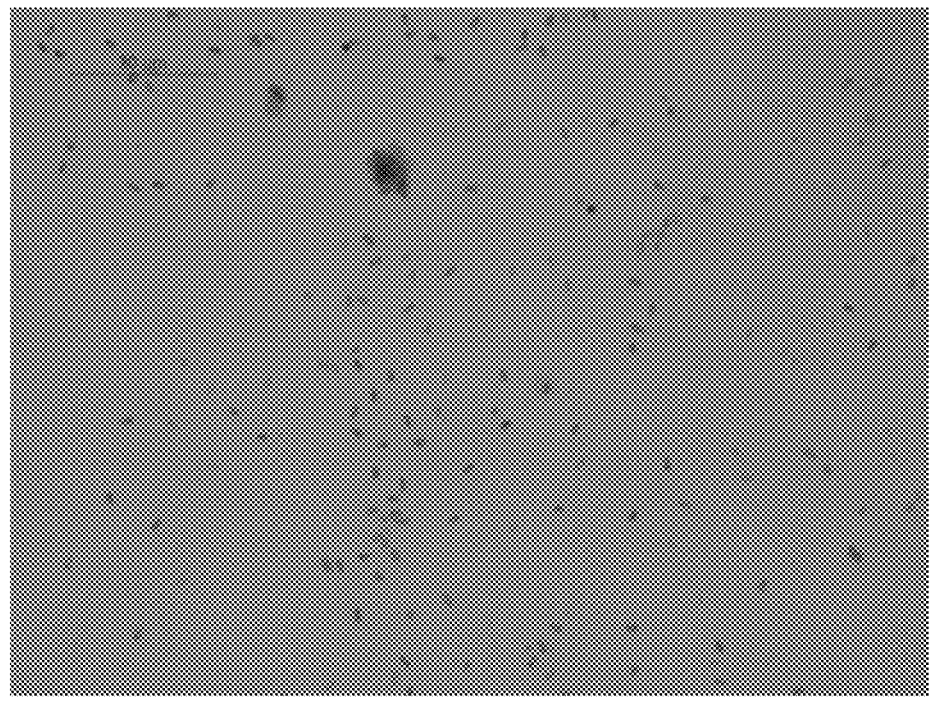
Figure 3A:
FIGS. 3A to 3C are the phylogenetic evolution diagrams of EO-degrading potential bacteria, wherein the EO-degrading potential bacteria were (FIG. 3A) *Acetobacter peroxydans* EO-01 original strain, (FIG. 3B) *Lactobacillus fermentum* EO-02 original strain, and (FIG. 3C) *Bacillus subtilis* EO-02 original strain obtained by the enrichment, purification and screening according to Example 1 of the present disclosure.
Figure 3B:
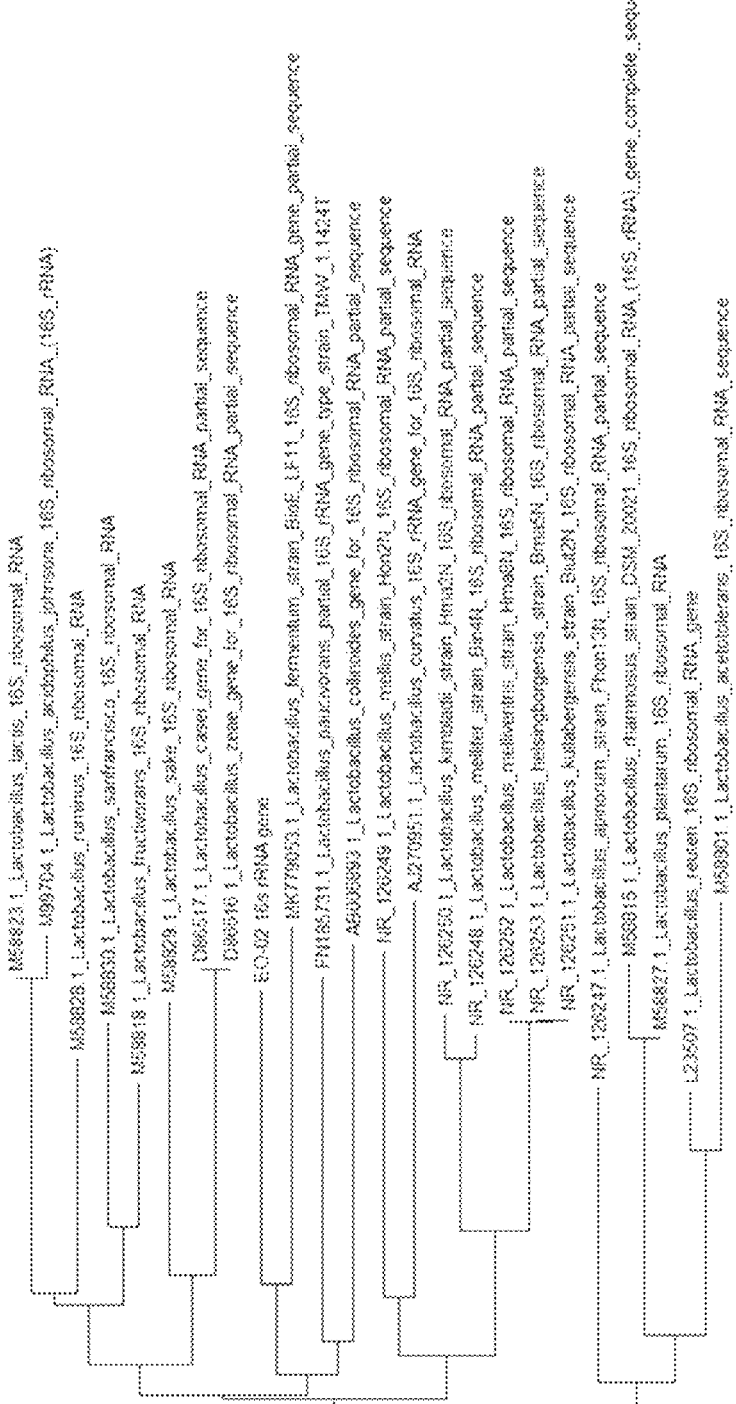
Figure 3C:
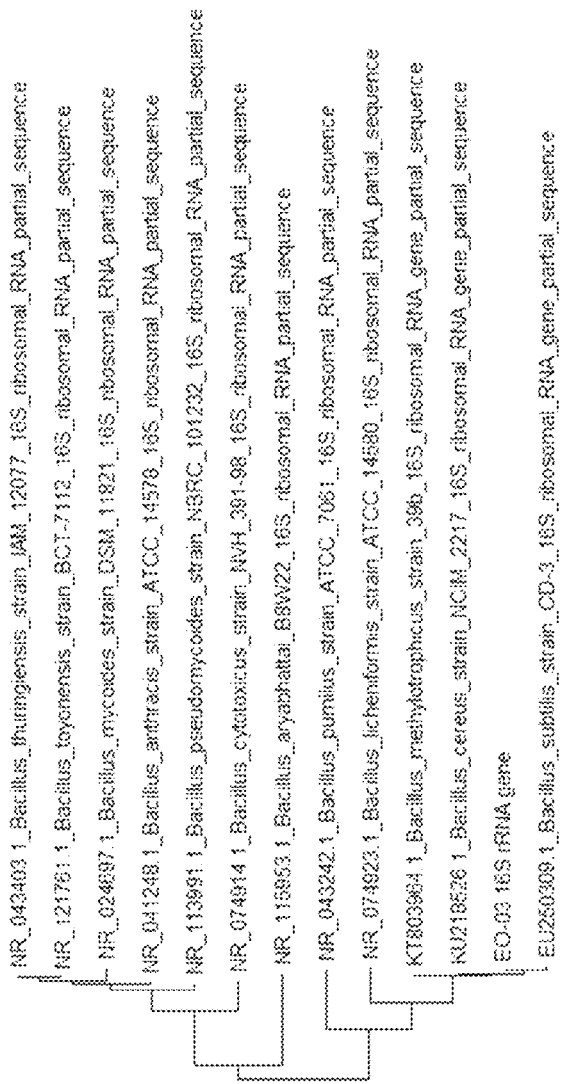
Figure 6A:
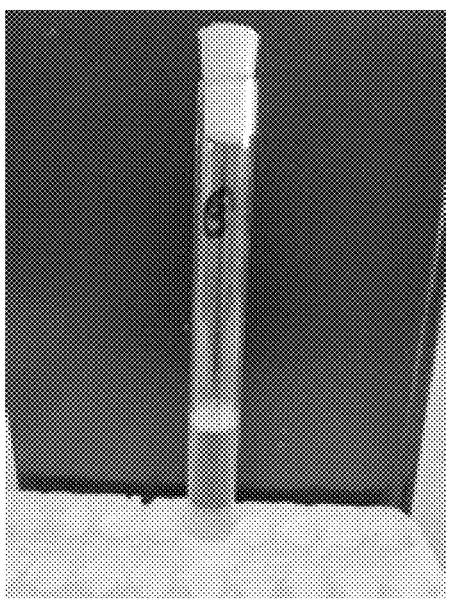
FIGS. 6A and 6B show bacterial colony growth of *Bacillus subtilis* EO-03 strain (FIG. 6A) after the inducted acclimation of Example 2, and (FIG. 6B) before the inducted acclimation of Example 2 in a liquid Sabouraud induction medium with 800 mg/L ethylene oxide after growing at a constant temperature of 37° C. for 48 hours in a comparative experiment of ethylene oxide degradation in Example 3 of the present disclosure.
Figure 6B:

The colony morphologies of the EO-01 original strain, EO-02 original strain, and EO-03 original strain are shown in FIGS. 1A, 1B and 1C, their Gram staining results shown in FIGS. 2A, 2B and 2C, and their phylogenetic trees shown in FIGS. 3A, 3B and 3C, respectively. According to the characterization results of morphology, physiology, biochemistry, and molecular biology, the EO-01 original strain was *Acetobacter peroxydans*, belonging to the genus *Acetobacter*; the EO-02 original strain was *Lactobacillus fermentum*, belonging to the genus *Lactobacillus*; and the EO-03 original strain was *Bacillus subtilis*, belonging to the genus *Bacillus*. The characterization and identification results of the three EO-degrading potential strains are summarized in Table 1 below.

TABLE 1

Characterization and identification results of EO-01 original strain, EO-02 original strain, and EO-03 original strain

| Strain | | EO-01 original strain | EO-02 original strain | EO-03 original strain |
|---|---|---|---|---|
| Colony morphology | | milky white needle-like petites, with gray or off-white cells, no pigment, smooth and moist surface, a round shape, regular edges, colony diameter of about 1.0 mm, | colorless and transparent, smooth and moist surface, round shape, regular edges, colony diameter from 0.5 mm to 1.0 mm, and no pigment | off-white or light yellow and opaque, rough surface, uneven edges, high viscosity, colony diameter from 4.0 mm to 5.0 mm, no pigment. |
| Microscopic morphology | | oval, or short straight rod shape | long straight rod shape, generally in the form of short-chain or binary fission. | oval shape, sporing. |
| Physiological and biochemical characteristics | Gram staining results | Gram-negative bacteria (red) | Gram-positive bacteria (purple) | Gram-positive bacteria (purple) |
| | Culture characteristics | strict aerobic bacteria, the most suitable growth temperature ranging from 20° C. to 35° C. | Facultative anaerobic bacteria, the most suitable growth temperature ranging from 30° C. to 40° C., good resistance to acid, well growth under acidic conditions . | Aerobic bacteria, extreme resistance to stress; Fast growth, relatively low nutritional requirements, capability of efficiently secreting many proteins and metabolites, and producing no toxins |
| 16s rDNA sequencing and sequence alignment results | | 16s rDNA is as listed in SEQ ID NO: 3, and has 99% homology with *Acetobacter peroxydans* 16S rDNA. | 16s rDNA is as listed in SEQ ID NO: 4, and has 99% homology with *Lactobacillus fermentum* 16S rDNA. | 16s rDNA is as listed in SEQ ID NO: 5, and has 99% homology with *Bacillus subtilis* 16S rDNA. |
| Strain identification results | | *Acetobacter peroxydans*, belonging to the genus *Acetobacter* | *Lactobacillus fermentum*, belonging to the genus *Lactobacillus* | *Bacillus subtilis*, belonging to the genus *Bacillus* |

Example 3 Induced Acclimation of Ethylene Oxide-Degrading Potential Bacteria

This is an example of induced acclimation of ethylene oxide-degrading potential bacteria strains, including induced acclimation of ethylene oxide tolerance and acclimation of ethylene oxide degradation ability.

Phase I: Induced Acclimation of Ethylene Oxide Tolerance

Four ethylene oxide-tolerance acclimation mediums containing different concentrations of ethylene oxide were prepared as follows: 10 g of peptone, 40 g of glucose, and 15 g of agar were dissolved in distilled water, and adjusted to pH 5.4-5.8, filling up to 1000 mL with distilled water and thoroughly mixed, dividing the prepared medium into portions of 250 mL and sterilized at 121° C. for 20 min; and, before use, heating the medium to melt, allowing to cool to about 50-56° C., and injecting 25 mg, 50 mg, 125 mg or 200 mg of ethylene oxide respectively with a sealed syringe to make ethylene oxide-tolerance acclimation medium plates with four different concentrations of ethylene oxide (100 mg/L, 200 mg/L, 500 mg/L or 800 mg/L), designated as ethylene oxide-tolerance acclimation medium plates A, B, C, and D, respectively.

Using the method of plate streaking, the three ethylene oxide-degrading potential bacteria, namely EO-01 original strain, EO-02 original strain, and EO-03 original strain, were inoculated into the ethylene oxide-tolerance acclimation medium plate A and incubated at a constant temperature of 37° C. for 48 h. Then a first single colony with the largest radius on each plate A was picked respectively and subcultured into the ethylene oxide-tolerance acclimation medium plate B and incubated at 37° C. for 48 h. Again, a second single colony with the largest colony radius on each plate B was picked respectively and subcultured into the ethylene oxide-tolerance acclimation medium plate C and incubated at a constant temperature of 37° C. for 48 hours. A third single colony with the largest colony radius on each plate C was picked and subcultured onto the ethylene oxide-tolerance acclimation medium plate D and incubated at a constant temperature of 37° C. for 48 hours. Then a fourth single colony with the largest colony radius on the plate D was picked and incubated at a constant temperature of 37° C. for 48 hours, to further obtain ethylene oxide-tolerance EO-01 strain, ethylene oxide-tolerance EO-02 strain, and ethylene oxide-tolerance EO-03 strain, respectively.

Phase II: Induced Acclimation of Ethylene Oxide Degradation Ability

Four ethylene oxide-degradation acclimation mediums containing a carbon source in different contents were prepared as follows: 10 g of peptone, glucose (20 g, 12 g, 4 g, or 0 g), and 15 g of agar were dissolved in distilled water, adjusted to pH 7.0-7.5, filled up to 1000 mL with distilled water and thoroughly mixing; dividing the medium prepared into 250 ml portions and sterilized at 121° C. for 20 min; and, before use, heating the medium to melt, allowing to cool to about 50-56° C., and injecting 200 mg of ethylene oxide with a sealed syringe to make Four ethylene oxide-degradation acclimation medium plates containing a carbon source in different contents (20 g/L 12 g/L, 4 g/L, and 0 g/L), designated as ethylene oxide-degradation acclimation medium plates A, B, C, and D, respectively.

Using the method of plate streaking, the ethylene oxide-tolerance EO-01 strain, ethylene oxide-tolerance EO-02 strain, and ethylene oxide-tolerance EO-03 strain were inoculated into the ethylene oxide-degradation acclimation medium plate A and incubated at a constant temperature of 37° C. for 48 hours, respectively. Then a first single colony with the largest radius on each plate A was picked respectively and subcultured into the ethylene oxide-degradation acclimation medium plate B and incubated at a constant temperature of 37° C. for 48 hours; a second single colony with the largest colony radius on each plate B was picked respectively and subcultured into the ethylene oxide-degradation acclimation medium plate C and incubated at a constant temperature of 37° C. for 48 hours; a third single colony with the largest colony radius on each plate C was picked respectively and subcultured into the ethylene oxide-degradation acclimation medium plate D and incubated at a constant temperature of 37° C. for 48 hours; a fourth single colony with the largest colony radius on each plate D was picked and stored on bevels made from agar medium containing nutrients corresponding to the ethylene oxide degradation acclimation medium plate D, so that strains with tolerance and degradation ability against ethylene oxide, namely *Acetobacter peroxydans* EO-01, *Lactobacillus fermentum* EO-02, and *Bacillus subtilis* EO-03, were obtained and deposited with Deposit numbers CGMCC No. 18431, CGMCC No. 18432, and CGMCC No. 18433 respectively.

The results of induced acclimation of ethylene oxide tolerance and degradation ability are shown in Table 2.

TABLE 2

Results of induced acclimation of ethylene oxide degradation ability

|  | Phase I | | | | Phase II | | | |
| --- | --- | --- | --- | --- | --- | --- | --- | --- |
| Carbon source (%) | 100 | 100 | 100 | 100 | 50 | 30 | 10 | 0 |
| EO concentration (mg/L) | 100 | 200 | 500 | 800 | 800 | 800 | 800 | 800 |
| EO-01 growth | + | + | + | + | + | + | + | + |
| EO-02 growth | + | + | + | + | + | + | + | + |
| EO-03 growth | + | + | + | + | + | + | + | + |

Note:
"+" represents bacterial growth.

The carbon source of 100%, 50%, 30%, 10%, and 0% in above table 2 corresponds to the glucose concentrations of 40 g/L, 20 g/L, 12 g/L, 4 g/L, and 0 g/L in ethylene oxide-degradation acclimation mediums, respectively.

The results in Table 2 show that the EO-01, EO-02, and EO-03 strains, after induced acclimation as described above, all grow well under the culture conditions with ethylene oxide as the only carbon source, and may use ethylene oxide as the carbon source.

According to the identification method described in Example 1, by morphological characterization, physiological and biochemical characterization, and molecular biological characterization, the EO-01, EO-02, and EO-03 strains were identified as follows:

The EO-01 strain after the inducted acclimation was *Acetobacter peroxydans*, belonging to the genus *Acetobacter*.

The EO-02 strain after the inducted acclimation was *Lactobacillus fermentum*, belonging to the genus *Lactobacillus*.

The EO-03 strain after the inducted acclimation was *Bacillus subtilis*, belonging to the genus *Bacillus*.

Example 4 Comparative Experiment of Ethylene Oxide Degradation

In the example below, comparative experiments were conducted to test the ability of the *Acetobacter peroxydans*

EO-01 strain, *Lactobacillus fermentum* EO-02 strain, and *Bacillus subtilis* EO-03 strain.

1. Experimental Method:

Liquid Sabouraud medium was prepared as follows: weighing 40 g of glucose, 5 g of casein trypsin digest, and 5 g of animal tissue pepsin digest, mixing in distilled water, adjusting to pH 5.4-5.8, and filling up to 1000 mL with distilled water; dividing the medium into portions of 250 mL in 500 mL Erlenmeyer flasks, sterilizing at 121° C. for 20 min, and allowing to cool to room temperature Two liquid Sabouraud induction medium with different ethylene oxide concentrations were made as follows: weighing 10 g peptone, filling up to 1000 mL with distilled water, mixing thoroughly; dividing into 400 mL portions, sterilizing at 121° C. for 20 min, and allowing to cool to room temperature; injecting 160 mg or 320 mg of ethylene oxide with a sealed syringe to make two liquid Sabouraud induction mediums containing ethylene oxide in different concentrations (400 mg/L and 800 mg/L respectively).

Culture and activation: ethylene oxide-degrading potential bacteria EO-01, EO-02, and EO-03 original strains, which were subjected to no induced acclimation according to Example 1, and EO-01, EO-02, and EO-03 strains after induced acclimation according to Example 2, were each inoculated at 10 µL into 100 mL of liquid Sabouraud medium, and incubated at 37° C. for 48 h with shaking at 200 rpm, so as to obtain activation solutions of EO-01, EO-02, and EO-03 original strains respectively and activation solutions of EO-01, EO-02, and EO-03 strains with a strain concentration from $10^{10}$ cfu/mL to $10^{12}$ cfu/mL in the each activation solutions, respectively.

To conduct a comparative experiment of ethylene oxide degradation, the following treatment and control groups were incubated in a 37° C. incubator for 48 hours.

Experimental group 1A (acclimated strains/800 mg/L ethylene oxide): 5 mL each of the activated solutions of the EO-01, EO-02, EO-03 strains after induced acclimation was inoculated in 400 mL of the liquid Sabouraud induction medium containing 800 mg/L ethylene oxide, with cell count in the medium being $10^8$-$10^{10}$ cfu/mL;

Experimental group 1B (unacclimated original strain/800 mg/L ethylene oxide): 5 mL each of the activated solutions of the EO-01, EO-02, EO-03 original strains before induced acclimation was inoculated in 400 mL of the liquid Sabouraud induction medium containing 800 mg/L ethylene oxide, with cell count in the medium being $10^8$-$10^{10}$ cfu/mL;

Control Group 1: Liquid Sabouraud induction medium containing 800 mg/L ethylene oxide without inoculation of any strain.

Experimental group 2A (acclimated strains/400 mg/L ethylene oxide): 5 mL each of the activated solutions of the EO-01, EO-02, EO-03 strains after induced acclimation was inoculated in 400 mL of the liquid Sabouraud induction medium containing 400 mg/L ethylene oxide, with cell count in the medium being $10^8$-$10^{10}$ cfu/mL;

Experimental group 2B (unacclimated original strain/400 mg/L ethylene oxide): 5 mL each of the activated solutions of the EO-01, EO-03, EO-03 original strains before induced acclimation was inoculated in 400 mL of the liquid Sabouraud induction medium containing 400 mg/L ethylene oxide, with cell count in the medium being $10^8$-$10^{10}$ cfu/mL;

Control group 2: Liquid Sabouraud induction medium containing 400 mg/L ethylene oxide without inoculation of any strain.

To calculate the concentrations of residual ethylene oxide and the degradation rates, samples were taken from the above Treatment groups and Control groups after the comparative test for gas chromatography analysis according to the methods described in "Sanitary Standards for Disposable Hygiene Products" (GB15979-2002) of China National Standards as follows:

a certain volume of pure ethylene oxide gas was collected with a sealed syringe and dissolved in deionized water to make a series of ethylene oxide standards of 0-1000 mg/L concentrations;

the subject samples to be analyzed were prepared by diluting samples from the treatment and control groups 5 times with deionized water;

after the Gas chromatography (GC) instrument is stabilized and under the same conditions, 2 µL each of the ethylene oxide standards and the diluted samples to be analyzed were injected into the GC instrument, wherein each sample was measured twice in parallel;

qualitive determination was conducted according to the retention time and quantitative calculation on each peak area was performed to take the average value;

an ethylene oxide standard curve was plotted according to the measurement data of the ethylene oxide standards, and the concentrations of residual ethylene oxide within each sample from the control and treatment groups were found based on the peak area corresponding to ethylene oxide thereof; and the degradation rate of ethylene oxide for each sample was calculated according to the following formula: Degradation Rate (%)=(Control Group Concentration—Treatment Group Concentration)/Control Group Concentration×100; specifically, the degradation rates of Treatment groups 1 and 2 were calculated based on Control Group 1, while those of Treatment groups 3 and 4 calculated based on Control Group 2.

Other details of the experiment include Column: Chromosorb 101HP60-80 mesh, glass column 2 m long, diameter 3 mm Column temperature: 120° C. Detector: 150° C., Gasifier: 150° C.; Carrier gas volume: Nitrogen: 35 ml/min, Hydrogen: 35 ml/min, Air: 350 ml/min, and the pre-column pressure is about 108 Kpa.

Additionally, promotion in the degradation ability for ethylene oxide of the strain before and after acclimation was calculated according to the following formula:

Promotion of degradation ability (%)=(Degradation Rate (%) of the strain after acclimation—Degradation Rate (%) of the strain before acclimation)/Degradation Rate (%) of the strain before acclimation.

2. Experimental Results

The experimental results are shown in Table 3 and FIGS. 4A to 6B. As shown in Table 3, *Acetobacter Peroxydans* EO-01 original strain, *Lactobacillus fermentum* EO-02 original strain, and *Bacillus subtilis* EO-03 original strain were acclimated to obtain outstanding resistance and significant degradability against high concentration of ethylene oxide, capable of degrading high concentration of ethylene oxide with no or low carbon source. Specifically, for 400 mg/L ethylene oxide, the EO-01, EO-02, and EO-03 strains after acclimation have degradation rates of 63.82%, 83.93%, and 72.96%, respectively, which were higher than the original strains before acclimation by 290.81%, 327.56%, and 319.31%, respectively; and for 800 mg/L ethylene oxide, EO-01, EO-02, and EO-03 strains after acclimation have degradation rates of 51.28%, 52.54%, and 57.19%, respectively, which were higher than the original strains before acclimation by 758.96%, 762.73%, and 545.5%, respectively.

TABLE 3

Comparative experiment results of ethylene oxide degradation by EO-01, EO-02 and EO-03 strains before and after induced acclimation

| Strain | EO concentration before test (mg/L) | EO concentration after test (mg/L) | | | Degradation rate (%) | | Promotion of degradation ability (%) |
| --- | --- | --- | --- | --- | --- | --- | --- |
| | | Before acclimation | After acclimation | Control group | Before acclimation | After acclimation | |
| EO-01 | 800 | 568.8 | 294.7 | 604.9 | 5.97% | 51.28% | 758.96% |
| | 400 | 192.2 | 83.1 | 229.7 | 16.33% | 63.82% | 290.81% |
| EO-02 | 800 | 566.1 | 286.1 | 602.8 | 6.09% | 52.54% | 762.73% |
| | 400 | 187.1 | 37.4 | 232.8 | 19.63% | 83.93% | 327.56% |
| EO-03 | 800 | 547.3 | 257.1 | 600.5 | 8.86% | 57.19% | 545.5% |
| | 400 | 190.3 | 62.3 | 230.4 | 17.40% | 72.96% | 319.31% |

Example 5—Treatment of Ethylene Oxide Sterilization Waste Gas

In general, ethylene oxide sterilization waste gas can be absorbed into water. The water containing the absorbed ethylene oxide can be contacted with a strain of the present invention in a method of biodegrading ethylene oxide. The water containing the absorbed ethylene oxide can be discharged or transferred to an anaerobic vessel, such as an anaerobic sewage tank. A strain of the present invention can then be added to the tank, thereby biodegrading the ethylene oxide.

In particular, 1) After the ethylene oxide sterilizer has sterilized, the ethylene oxide sterilization exhaust gas generated is fed into a hydration system, which uses the internal circulating water to absorb the incoming ethylene oxide sterilization exhaust gas, and several cycles of absorption produce ethylene oxide wastewater containing ethylene oxide.

(2) The waste water was passed into an anaerobic ethylene oxide treatment cell inoculated with EO-01, EO-02, and EO-03 strains, the strain concentration was $10^{10}$-$10^{12}$ cfu/mL, the inoculation amount was 1%-2%, the strain(s) used the active sludge in the anaerobic ethylene oxide treatment cell as the culture, and ethylene oxide was used as the carbon source and energy for metabolism, growth and proliferation, thus achieving the purpose of ethylene oxide treatment.

The wastewater was treated in an anaerobic biological ethylene oxide treatment cell inoculated with the strain mixture, the mixture in the treatment cell was continuously stirred, the temperature was controlled at 32° C.-42° C. and the treatment time was 48 hours. The residual concentration of ethylene oxide in the treated wastewater was 25.89 mg/L with a treatment efficiency of 85.64%.

The above concentrations were detected by gas chromatography in accordance with GB 15979-2002 (Appendix D), which is explained above. The degradation rate was calculated according to the following formula: Degradation rate= (starting concentration−residual concentration)/starting concentration.

As another practical application, activated sludge can be contacted with a strain of the present invention, thereby biodegrading ethylene oxide in the activated sludge.

Comparative tests and applications may be carried out in other samples containing ethylene oxide, such as sewage, sludge, exhaust gas, or wastewater, such as industrial (including industries related to petroleum and derivative products), medical treatment (such as ethylene oxide sterilant) and other sewage, sludge, exhaust gas, or wastewater using strains of the invention In the above-described tests and applications, the degradation rate is at least 10%, 15%, 20%, 25%, 30%, 35%, 40%, 50%, 60%, 70%, 75%, 80%, 90%, 95%, 100%, 125%, 150%, 200%, 250%, 300%, 350%, 400%, 450%, 500%, 550%, 600%, 650%, 700%, 750%, 800%, 850%, 900%, 1000%, 1100%, 1200%, 1300%, 1400%, or 1500% greater relative to the degradation rate of ethylene oxide in the absence of the *Acetobacter peroxydans* strain EO-01, the *Lactobacillus fermentum* strain EO-02; the *Bacillus subtilis* strain EO-03, the *Alcaligenes faecalis* strain EO-05 or *Alcaligenes faecalis* strain comprising the 16S rDNA sequence of SEQ ID NO: 6, the *Acetobacter peroxydans* strain with the 16S rDNA of SEQ ID NO: 3; the *Lactobacillus fermentum* strain with the 16S rDNA of SEQ ID NO: 4; or the *Bacillus subtilis* strain with the 16S rDNA of SEQ ID NO: 5.

The detailed embodiments described herein are only for the purpose of illustrating the present disclosure and are not intended to limit the scope of the present disclosure in any way. It would be understood by a person skilled in the art that various changes and modifications can be made to the embodiments described herein without departing from the scope and spirit of the present disclosure. Such changes and modifications are contemplated by the present disclosure, the scope of which should only be defined by the following claims.

What is claimed is:

1. A product which is a
   a bacterial strain *Lactobacillus fermentum* EO-02 with Deposit number of CGMCC No. 18432 capable of degrading ethylene oxide.

2. The product according to claim 1, wherein the bacterial strain has a concentration from $10^{10}$ cfu/mL to $10^{12}$ cfu/mL.

3. The product according to claim 1, wherein the *Lactobacillus fermentum* EO-02 with Deposit number of CGMCC No. 18432 is capable of degrading ethylene oxide in sewage, sludge, or exhaust gas.

4. The product according to claim 1, wherein the *Lactobacillus fermentum* EO-02 with Deposit number of CGMCC No. 18432 is capable of degrading ethylene oxide at a rate at least 10% greater relative to the degradation rate of ethylene oxide in the absence of *Lactobacillus fermentum* EO-02 with Deposit number of CGMCC No. 18432.

5. The product according to claim 1, wherein the *Lactobacillus fermentum* EO-02 with Deposit number of CGMCC No. 18432 strain bacterium is capable of using ethylene oxide as a carbon source and is capable of growing normally with ethylene oxide as the main carbon source in the culture.

* * * * *

SEQUENCE LISTING

<160> NUMBER OF SEQ ID NOS: 7

<210> SEQ ID NO 1
<211> LENGTH: 20
<212> TYPE: DNA
<213> ORGANISM: Artificial Sequence
<220> FEATURE:
<223> OTHER INFORMATION: Synthetic construct

<400> SEQUENCE: 1

```
agagtttgat cctggctcag                                              20
```

<210> SEQ ID NO 2
<211> LENGTH: 19
<212> TYPE: DNA
<213> ORGANISM: Artificial Sequence
<220> FEATURE:
<223> OTHER INFORMATION: Synthetic construct

<400> SEQUENCE: 2

```
ggttaccttg ttacgactt                                               19
```

<210> SEQ ID NO 3
<211> LENGTH: 1412
<212> TYPE: DNA
<213> ORGANISM: Acetobacter peroxydans

<400> SEQUENCE: 3

```
agagtttgat catggctcag agcgaacgct ggcggcatgc ttaacacatg caagtcgcac    60
gaaggtttcg gccttagtgg cggacgggtg agtaacgcgt aggaatctat ccatgggtgg   120
gggataacac tgggaaactg gtgctaatac cgcatgacac ctgagggtca aggcgcaag    180
tcgcctgtgg aggagcctgc gttcgattag ctagttggtg gggtaaaggc ctaccaaggc   240
gatgatcgat agctggtttg agaggatgat cagccacact gggactgaga cacggcccag   300
actcctacgg gaggcagcag tggggaatat tggacaatgg gggcaaccct gatccagcaa   360
tgccgcgtgt gtgaagaagg tcttcggatt gtaaagcact tcgacgggga cgatgatga   420
cggtacccgt agaagaagcc ccggctaact tcgtgccagc agccgcggta atacgaaggg   480
ggctagcgtt gctcggaatg actgggcgta aagggcgtgt aggcggtttt gacagtcaga   540
tgtgaaatcc ccgggcttaa cctgggagct gcatttgaga cgttaagact agagtgtgag   600
agagggttgt ggaattccca gtgtagaggt gaaattcgta gatattggga agaacaccgg   660
tggcgaaggc ggcaacctgg ctcattactg acgctgaggc gcgaaagcgt ggggagcaaa   720
caggattaga taccctggta gtccacgctg taaacgatgt gtgctagatg ttgggtaact   780
tagttactca gtgtcgcagt taacgcgtta agcacaccgc ctggggagta cggccgcaag   840
gttgaaactc aaaggaattg acgggggccc gcacaagcgg tggagcatgt ggtttaattc   900
gaagcaacgc gcagaacctt accagggctt gaatgtggag gctgtaggca gagatgtcta   960
tttcttcgga cctccaacac aggtgctgca tggctgtcgt cagctcgtgt cgtgagatgt  1020
tgggttaagt cccgcaacga gcgcaacccc tatctttagt tgccagcatg tttgggtggg  1080
cactctagag agactgccgg tgacaagccg gaggaaggtg gggatgacgt caagtcctca  1140
tggcccttat gtcctgggct acacacgtgc tacaatggcg gtgacagtgg gaagctatgt  1200
ggtgacacag tgctgatctc taaaagccgt ctcagttcgg attgcactct gcaactcgag  1260
tgcatgaagg tggaatcgct agtaatcgcg gatcagcatg ccgcggtgaa tacgttcccg  1320
ggccttgtac acaccgcccg tcacaccatg ggagtggttt gaccttaagc cggtgagcga  1380
accgcaagga cgcagccgac cacgtcgtcg ct                                1412
```

<210> SEQ ID NO 4
<211> LENGTH: 1453
<212> TYPE: DNA
<213> ORGANISM: Lactobacillus fermentum

<400> SEQUENCE: 4

```
gcggctggct cctaaaaggt taccccaccg actttgggtg ttacaaactc tcatggtgtg      60
acgggcggtg tgtacaaggc ccgggaacgt attcaccgcg gcatgctgat ccgcgattac     120
tagcgattcc gacttcgtgc aggcgagttg cagcctgcag tccgaactga aacggttttt    180
aagagatttg cttgccctcg cgagttcgcg actcgttgta ccgtccattg tagcacgtgt     240
gtagcccagg tcataagggg catgatgatc tgacgtcgtc cccaccttcc tccggtttgt     300
caccggcagt ctcactagag tgcccaactt aatgctggca actagtaaca agggttgcgc     360
tcgttgcggg acttaaccca acatctcacg acacgagctg acgacgacca tgcaccacct    420
gtcattgcgt tcccgaagga aacgccctat ctctagggtt ggcgcaagat gtcaagacct     480
ggtaaggttc ttcgcgtagc ttcgaattaa accacatgct ccaccgcttg tgcgggcccc     540
cgtcaattcc tttgagtttc aaccttgcgg tcgtactccc caggcggagt gcttaatgcg     600
ttagctccgg cactgaaggg cggaaaccct ccaacaccta gcactcatcg tttacggcat     660
ggactaccag ggtatctaat cctgttcgct acccatgctt tcgagtctca gcgtcagttg     720
cagaccaggt agccgccttc gccactggtg ttcttccata tatctacgca ttccaccgct     780
acacatggag ttccactacc ctcttctgca ctcaagttat ccagtttccg atgcacttct     840
ccggttaagc cgaaggcttt cacatcagac ttagaaaacc gcctgcactc tctttacgcc     900
caataaatcc ggataacgct tgccacctac gtattaccgc ggctgctggc acgtagttag     960
ccgtgacttt ctggttaaat accgtcaacg tatgaacagt tactctcata cgtgttcttc    1020
tttaacaaca gagctttacg agccgaaacc cttcttcact cacgcggtgt tgctccatca    1080
ggcttgcgcc cattgtggaa gattccctac tgctgcctcc cgtaggagta tgggccgtgt    1140
ctcagtccca ttgtggccga tcagtctctc aactcggcta tgcatcatcg ccttggtagg    1200
ccgttacccc accaacaagc taatgcaccg caggtccatc cagaagtgat agcgagaagc    1260
catcttttaa gcgttgttca tgcgaacaac gctgttatgc ggtattagca tctgtttcca    1320
aatgttgtcc cccgcttctg ggcaggttac ctacgtgtta ctcacccgtc cgccactcgt    1380
tggcgaccaa aatcaatcag gtgcaagcac catcaatcaa ttgggccaac gcgttcgact    1440
gcattattag gca                                                       1453
```

<210> SEQ ID NO 5
<211> LENGTH: 1439
<212> TYPE: DNA
<213> ORGANISM: Bacillus subtilis

<400> SEQUENCE: 5

```
ctatacatgc aagtcgagcg gacagatggg agcttgctcc ctgatgttag cggcggacgg      60
gtgagtaaca cgtgggtaac ctgcctgtaa gactgggata actccgggaa accgggctaa    120
ataccggatg gttgtttgaa ccgcatggtt cagacataaa aggtggcttc ggctaccact     180
tacagatgga cccgcggcgc attagctagt tggtgaggta acggctcacc aaggcgacga     240
tgcgtagccg acctgagagg gtgatcggcc acactgggac tgagacacgg cccagactcc    300
tacgggaggc agcagtaggg aatcttccgc aatggacgaa agtctgacgg agcaacgccg     360
cgtgagtgat gaaggttttc ggatcgtaaa gctctgttgt tagggaagaa caagtgccgt    420
tcaaataggg cggcaccttg acggtaccta accagaaagc cacggctaac tacgtgccag    480
cagccgcggt aatacgtagg tggcaagcgt tgtccggaat tattgggcgt aaagggctcg     540
caggcggttt cttaagtctg atgtgaaagc ccccggctca accggggagg gtcattggaa    600
```

| | |
|---|---:|
| actgggggaac ttgagtgcag aagaggagag tggaattcca cgtgtagcgg tgaaatgcgt | 660 |
| agagatgtgg aggaacacca gtggcgaagg cgactctctg gtctgtaact gacgctgagg | 720 |
| agcgaaagcg tggggagcga acaggattag ataccctggt agtccacgcc gtaaacgatg | 780 |
| agtgctaagt gttaggggggt ttccgcccct tagtgctgca gctaacgcat taagcactcc | 840 |
| gcctggggag tacggtcgca agactgaaac tcaaaggaat tgacgggggc cgcacaagc | 900 |
| ggtgagcat gtggtttaat tcgaagcaac gcgaagaacc ttaccaggtc ttgacatcct | 960 |
| ctgacaatcc tagagatagg acgtcccctt cgggggcaga gtgacaggtg gtgcatggtt | 1020 |
| gtcgtcagct cgtgtcgtga gatgttgggt taagtcccgc aacgagcgca acccttgatc | 1080 |
| ttagttgcca gcattcagtt gggcactcta aggtgactgc cggtgacaaa ccggaggaag | 1140 |
| gtggggatga cgtcaaatca tcatgcccct tatgacctgg gctacacacg tgctacaatg | 1200 |
| ggcagaacaa agggcagcga aaccgcgagg ttaagccaat cccacaaatc tgttctcagt | 1260 |
| tcggatcgca gtctgcaact cgactgcgtg aagctggaat cgctagtaat cgcggatcag | 1320 |
| catgccgcgg tgaatacgtt cccgggcctt gtacacaccg cccgtcacac cacgagagtt | 1380 |
| tgtaacaccc gaagtcggtg aggtaacctt ttaggagcca gccgccgaag gttggacag | 1439 |

<210> SEQ ID NO 6
<211> LENGTH: 1432
<212> TYPE: DNA
<213> ORGANISM: Alcaligenes faecalis

<400> SEQUENCE: 6

| | |
|---|---:|
| gctttaacac atgcaagtcg aacgcagca cgcagagagc ttgctctctt ggtggcgagt | 60 |
| ggcggacggg tgagtaatat atcggaacgt gcccagtagc gggggataac tactcgaaag | 120 |
| agtggctaat accgcatacg ccctacgggg gaaaggggggg gatcgcaaga cctctcacta | 180 |
| ttggagcggc cgatatcgga ttagctagtt ggtggggtaa aggctcacca aggcaacgat | 240 |
| ccgtagctgt tttgagagga cgaccagcca cactgggact gagacacggc ccagactcct | 300 |
| acgggaggca gcagtgggga attttggaca atgggggaaa ccctgatcca gccatcccgc | 360 |
| gtgtatgatg aaggccttcg ggttgtaaag tacttttggc agagaagaaa aggcatcccc | 420 |
| taatacggga tgctgctgac ggtatctgca gaataagcac cggctaacta cgtgccagca | 480 |
| gccgcggtaa tacgtagggt gcaagcgtta atcggaatta ctgggcgtaa agcgtgtgta | 540 |
| ggcggttcgg aaagaaagat gtgaaatccc agggctcaac cttggaactg cattttttaac | 600 |
| tgccgagcta gagtatgtca gagggggggta gaattccacg tgtagcagtg aaatgcgtag | 660 |
| atatgtggag gaataccgat ggcgaaggca gcccctggg ataatactga cgctcagaca | 720 |
| cgaaagcgtg gggagcaaac aggattagat accctggtag tccacgccct aaacgatgtc | 780 |
| aactagctgt tggggccgtt aggccttagt agcgcagcta acgcgtgaag ttgaccgcct | 840 |
| ggggagtacg gtcgcaagat taaaactcaa aggaattgac ggggacccgc acaagcggtg | 900 |
| gatgatgtgg attaattcga tgcaacgcga aaaaccttac ctacccttga catgtctgga | 960 |
| aagccgaaga gatttggcag tgctcgcaag agaaccggaa cacaggtgct gcatggctgt | 1020 |
| cgtcagctcg tgtcgtgaga tgttgggtta agtcccgcaa cgagcgcaac ccttgtcatt | 1080 |
| agttgctacg caagagcact ctaatgagac tgccggtgac aaaccggagg aaggtgggga | 1140 |
| tgacgtcaag tcctcatggc ccttatgggt agggcttcac acgtcataca atggtcggga | 1200 |
| cagagggtcg ccaaccccgcg aggggggagcc aatctcagaa acccgatcgt agtccggatc | 1260 |
| gcagtctgca actcgactgc gtgaagtcgg aatcgctagt aatcgcggat cagaatgtcg | 1320 |

-continued

```
cggtgaatac gttcccgggt cttgtacaca ccgcccgtca caccatggga gtgggtttca    1380
ccagaagtag gtagcctaac cgcaaggagg gcgctaccac ggtgatgatg tc            1432

<210> SEQ ID NO 7
<211> LENGTH: 1438
<212> TYPE: DNA
<213> ORGANISM: Enterococcus faecium EO-04

<400> SEQUENCE: 7
gcggctggct ccaaaaggtt acctcaccga cttcgggtgt tacaaactct cgtggtgtga      60
cgggcggtgt gtacaaggcc cgggaacgta ttcaccgcgg cgtgctgatc cgcgattact    120
agcgattccg gcttcatgca ggcgagttgc agcctgcaat ccgaactgag agaagcttta    180
agagattagc ttagcctcgc gacttcgcaa ctcgttgtac ttcccattgt agcacgtgtg    240
tagcccaggt cataagggggc atgatgattt gacgtcatcc ccaccttcct ccggtttgtc    300
accggcagtc ttgctagagt gcccaactga atgatggcaa ctaacaataa gggttgcgct    360
cgttgcggga cttaacccaa catctcacga cacgagctga cgacaaccat gcaccacctg    420
tcactttgcc cccgaagggg aagctctatc tctagagtgg tcaaaggatg tcaagacctg    480
gtaaggttct tcgcgttgct tcgaattaaa ccacatgctc caccgcttgt gcgggccccc    540
gtcaattcct ttgagtttca accttgcggt cgtactcccc aggcggagtg cttaatgcgt    600
tagctgcagc actgaagggc ggaaaccctc caacacttag cactcatcgt ttacggcgtg    660
gactaccagg gtatctaatc ctgtttgctc cccacgcttt cgagcctcag cgtcagttac    720
agaccagaga gccgccttcg ccactggtgt tcctccatat atctacgcat ttcaccgcta    780
cacatggaat tccactctcc tcttctgcac tcaagtctcc cagtttccaa tgaccctccc    840
cggttgagcc ggggggcttc acatcagact taagaaaccg cctgcgctcg ctttacgccc    900
aataaatccg gacaacgctt gccacctacg tattaccgcg gctgctggca cgtagttagc    960
cgtggctttc tggttagata ccgtcaaggg atgaacagtt actctcatcc ttgttcttct   1020
ctaacaacag agttttacga tccgaaaacc ttcttcactc acgcggcgtt gctcggtcag   1080
actttcgtcc attgccgaag attccctact gctgcctccc gtaggagttt gggccgtgtc   1140
tcagtcccaa tgtggccgat caccctctca ggtcggctat gcatcgtggc cttggtgagc   1200
cgttacctca ccaactagct aatgcaccgc gggtccatcc atcagcgaca cccgaaagcg   1260
cctttcaaat caaaaccatg cggttttgat tgttatacgg tattagcacc tgtttccaag   1320
tgttatcccc ttctgatggg caggttaccc acgtgttact cacccgttcg ccactcctct   1380
ttttccggtg gagcaagctc cggtggaaaa agaagcgtgc gacttgcacg tattaggc     1438
```